United States Patent [19]

Kesling et al.

[11] Patent Number: 4,900,250

[45] Date of Patent: Feb. 13, 1990

[54] ELASTIC ORTHODONTIC APPLIANCE FOR AN EDGEWISE-TYPE BRACKET

[75] Inventors: Peter C. Kesling; Dennis B. Henderlong, both of LaPorte, Ind.

[73] Assignee: TP Orthodontics, Inc., Westville, Ind.

[21] Appl. No.: 176,256

[22] Filed: Apr. 14, 1988

Related U.S. Application Data

[63] Continuation-in-part of Ser. No. 44,908, Apr. 30, 1987, abandoned.

[51] Int. Cl.$^4$ .............................................. A61C 7/00
[52] U.S. Cl. ......................................... 433/11; 433/18
[58] Field of Search ........................ 433/10, 11, 13, 18

[56] References Cited

U.S. PATENT DOCUMENTS

| | | | |
|---|---|---|---|
| 2,767,469 | 10/1956 | Gladstone | 433/11 |
| 3,641,672 | 2/1972 | Kesling | 32/14 A |
| 3,686,758 | 8/1972 | Kesling | 32/14 A |
| 3,879,850 | 4/1975 | Wallshein | 32/14 A |
| 4,054,997 | 10/1977 | Wallshein | 32/14 A |
| 4,217,686 | 8/1980 | Dragan | 433/13 X |
| 4,340,363 | 7/1982 | Klein et al. | 433/18 |
| 4,531,911 | 7/1985 | Creekmore | 433/8 |

Primary Examiner—Robert P. Swiatek
Assistant Examiner—Nicholas D. Lucchesi
Attorney, Agent, or Firm—Lloyd L. Zickert

[57] ABSTRACT

An elastic orthodontic appliance for use with an edgewise-type bracket having an archwire slot with tipping and uprighting surfaces. The elastic appliance functions as a ligature to provide the usual function of retaining an archwire in the archwire slot of the bracket and additionally functions as a force transmitting device to provide supplementary tipping or uprighting forces between the bracket and the archwire. The appliance includes a ring portion having a transverse web or cross member and in some embodiments enlargements that are forced between the archwire and either the tipping or uprighting surfaces or the lateral sides of the bracket and sized to be compressed so that a force is generated between the archwire and the bracket.

26 Claims, 4 Drawing Sheets

ELASTIC ORTHODONTIC APPLIANCE FOR AN EDGEWISE-TYPE BRACKET

DESCRIPTION

This is a continuation-in-part of my copending application Ser. No. 044,908, filed Apr. 30, 1987 now abandoned.

This invention relates in general to an elastic orthodontic appliance for use with an edgewise-type bracket capable of tipping or uprighting movement along an archwire, and more particularly to an elastic orthodontic appliance functioning as a ligature to connect an archwire to a bracket and/or also functioning as a supplementary force transmission device to produce tipping or uprighting forces.

The terms "tipping" and "uprighting" relate to movements of teeth caused by the application of selected forces. Generally, "tipping" refers to either labial-lingual or mesial-distal movement of the crown of a tooth, while "uprighting" refers to either mesial or distal movement of the tip (apex) of the root of a tooth. Tipping herein will be in the mesial-distal direction unless otherwise specified. Torque generally refers to the movement of the root of a tooth in the labial-lingual direction as a result of forces being applied to the crown of the tooth. Thus, crown movement will be referred to as tipping, while root movement will be referred to as uprighting or torquing. The use of "and/or" herein is intended to cover three alternatives. For example, "mesial and/or distal archwire stops" means mesial and distal archwire stops or mesial archwire stops or distal archwire stops.

BACKGROUND OF THE INVENTION

Heretofore, it has been well known to use elastic ligatures for connecting archwires to edgewise-type brackets. An elastic ligature used for fastening an archwire in the horizontal slot of an edgewise-type bracket produces a unique "hammock effect" on the bracket. This may also be considered a centering action, as the ligature extends over and partially around the archwire at each of the mesial and distal sides of the bracket, while at the same time being hooked over the gingival and occlusal tie wing tips and there held lingual to the labial side of the archwire. Thus, this effect tends to urge the bracket to a position relative to the archwire where the archwire will be substantially centered in the archwire slot. Yet, this action caused by the "hammock effect" cannot be relied upon to positively move the bracket, and it is necessary to rely on other means to provide positive movement and control.

It has also been known to provide an edgewise-type bracket capable of allowing free crown tipping and a predetermined degree of root uprighting. This type of bracket is disclosed in copending Peter C. Kesling application Ser. No. 054,837, filed June 4, 1987, and entitled "Edgewise Bracket To Provide Both Free Crown Tipping And A Predetermined Degree of Root Uprighting". As also disclosed in this application, it is known to use an elastic orthodontic appliance in the form of a ring with enlargements for the purpose of inducing additional forces between the archwire and a bracket. While that elastic appliance is in the form of a ring and having enlargements that are intended to supplement a tipping or uprighting force transmitting device, it has been found that it is not entirely satisfactory to provide the desired supplemental force.

SUMMARY OF THE INVENTION

The present invention obviates the above mentioned difficulties of using elastic orthodontic appliances for connecting archwire to brackets and for applying supplementary moving forces in providing a new and improved elastic orthodontic appliance that is capable of producing more positive supplementary tipping or uprighting forces.

The appliance generally includes a ring portion and a diametrically disposed cross member or web, and it may additionally include nodules or enlargements on the ring portion or cross member.

Inasmuch as elastic orthodontic appliances of the type according to the invention are very small as all appliances are that are used in the mouth and mounted on teeth, it is difficult to mount heretofore known appliances with force transmitting nodules and be assured that the nodules are in proper orientation between the archwire and the bracket to provide the desired transmission of forces. The present invention overcomes this problem in allowing the orthodontist to easily observe when the force transmitting nodules are properly oriented by including a cross member or web, the location of which is across the face of the bracket when the appliance is mounted on the bracket and the location of which indicates visually the orientation and placement of the force transmission nodules.

The cross member or web of the present appliance having nodules further serves to more positively locate the force transmitting nodules between the appropriate bracket surfaces and the archwire so as to produce the desired transmission forces.

It is therefore an object of the present invention to provide a new and improved elastic orthodontic appliance for connecting an archwire to edgewise-type brackets and for producing supplementary tipping or uprighting forces.

Another object of the present invention is in the provision of a new and improved elastic orthodontic appliance for producing supplementary tipping or uprighting forces which includes an endless strand with a cross member.

A further object of the present invention is to provide a new and improved elastic orthodontic appliance for producing supplementary tipping or uprighting forces which includes an endless strand with a cross member and one or more nodules aligned with the cross member.

Another object of the present invention is in providing a new and improved elastic orthodontic appliance for use on edgewise-type brackets capable of allowing both tipping or uprighting movements of a tooth along an archwire wherein the appliance includes an endless strand with a cross member and force transmitting nodules in alignment with the cross member so as to visually indicate the location of the nodules at each end of the cross member when located only on the lingual surface of the appliance and not normally visible during the application of an appliance to a bracket.

A further object of the present invention is in the provision of a new and improved elastic orthodontic appliance functioning as a ligature and a force generating device and which generally overcomes the "hammock effect" of a standard elastic ligature when used to connect an archwire to a bracket capable of permitting tipping or uprighting movement relative to the archwire.

Another object of the present invention is in the provision of a new and improved elastic orthodontic appliance which functions to connect an archwire to a bracket and is useful on a bracket capable of permitting free tipping or uprighting relative to the archwire and which includes force transmission nodules that can also serve to maintain the bracket at a given position relative to the archwire.

Other objects, features and advantages of the invention will be apparent from the following detailed disclosure, taken in conjunction with the accompanying sheets of drawings, wherein like reference numerals refer to like parts.

DESCRIPTION OF THE INVENTION

Figures 12, 13:
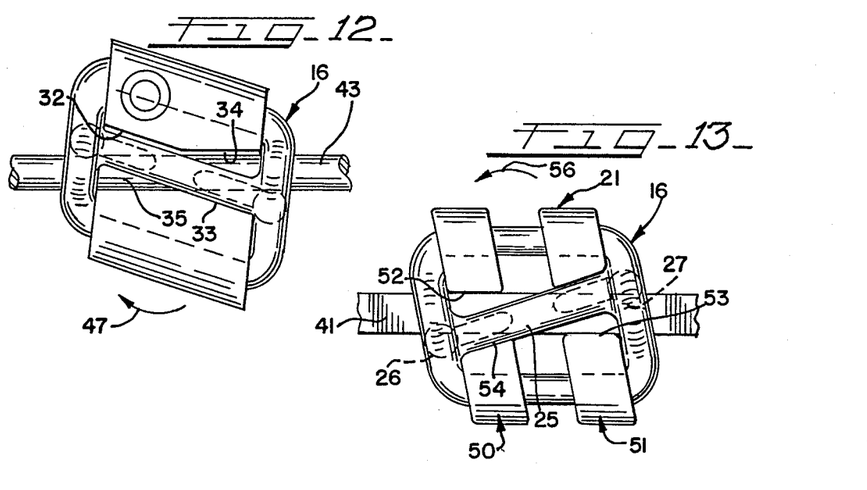
FIG. 12 is a front or labial elevational view like FIG. 7 but omitting the uprighting spring and showing the location of the force nodules to effect a tipping or uprighting force.
FIG. 13 is a front elevational view showing a modified bracket on which the elastic orthodontic appliance of the present invention is mounted for retaining the archwire in place and for effecting supplementary uprighting movement.
Figure 15:
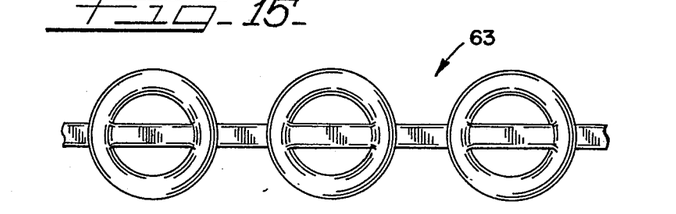
FIG. 15 is a front elevational view of a further modification of the appliance in chain form which differs from FIG. 14 in the orientation of the cross bar.
Figures 16, 17:
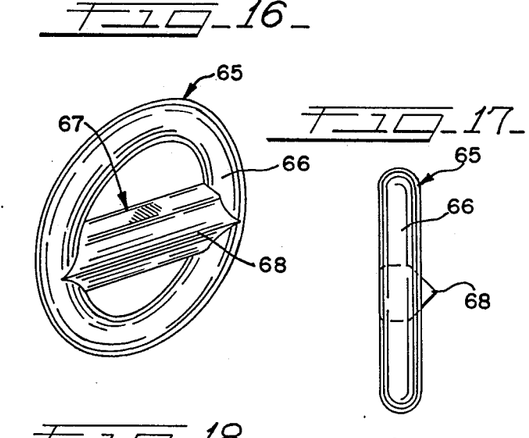
FIG. 16 is a perspective view of the backside of a further modification of the elastic appliance of the invention which does not include any nodules.
FIG. 17 is a side elevational view of the appliance of FIG. 16.
Figure 18:
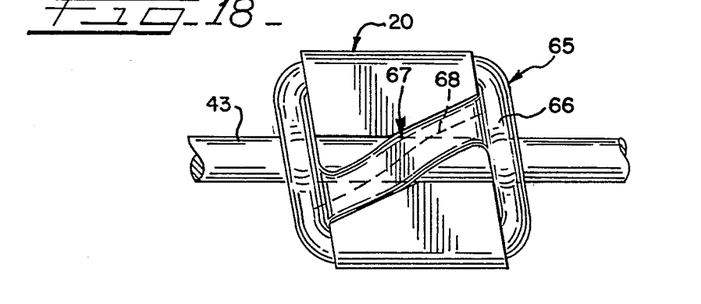
FIG. 18 is a front elevational view of the appliance of FIGS. 16 and 17 and illustrated in mounting relation on a bracket and in combination with an archwire.
Figure 19:
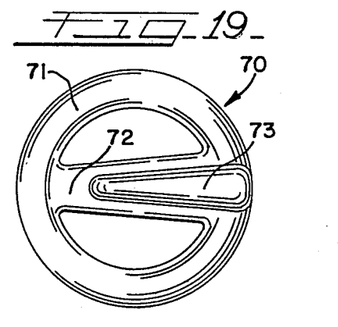
FIG. 19 is a rear elevational view of a modified elastic appliance with a single force transmitting nodule.
Figure 20:
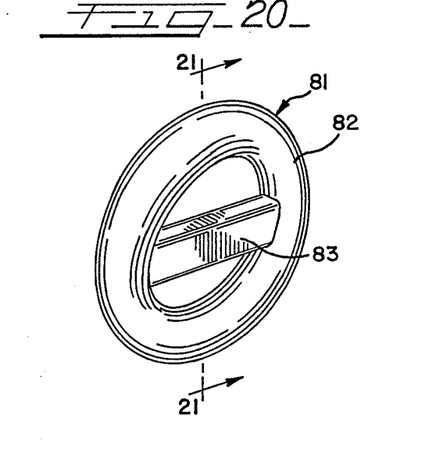
FIG. 20 is a front perspective view of a further modification of the invention which differs from the other embodiments in that the appliance is lugless.

The improved elastic orthodontic appliance of the present invention, generally indicated by the numeral 16, is shown in its unstretched condition in FIGS. 1 to 6, prior to mounting on a bracket, and in use in stretched condition in mounting relation on a bracket in FIGS. 7 to 13. The appliance is shown in chain form in FIGS. 14 and 15, and a no-nodule modification is illustrated in FIGS. 16 to 18. Another form of ring with a single nodule is shown in FIG. 19. A lugless or nodule-less ring is shown in FIGS. 20 to 23, and a modification of the ring of FIG. 20 is shown in FIG. 24. The bracket shown in FIGS. 7 to 12 is a single wing edgewise-type bracket, generally indicated by the numeral 20, and having an archwire slot for receiving an archwire of rectangular or round configuration and for permitting tipping or uprighting movements along the archwire. A twin or double tie wing bracket of the same type in combination with the appliance of the invention is shown in FIG. 13 and generally designated by the numeral 21, and which includes a pair of tie wing tips on each side of the archwire slot, such as a bracket having one tip on one side and two tips on the other side. Any of the ring variations illustrated may be used with either the single wing or double wing brackets.

For simplicity purposes, the brackets illustrated are not mounted on bases, pads or bands, but it will be assumed that they will be secured to such bases, pads or bands which then in turn function to permit bonding or cementing in the usual manner to a tooth surface.

Figures 1, 2, 3, 4, 5, 6:
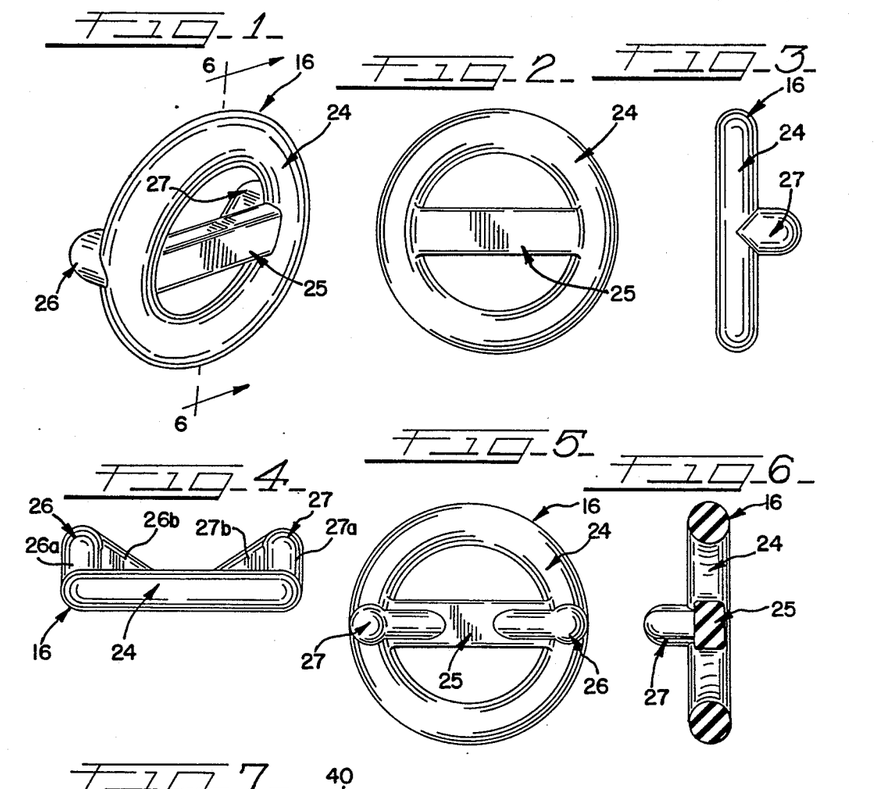
FIG. 1 is a perspective view of the elastic orthodontic appliance of the present invention.
FIG. 2 is a front or labial view of the appliance of FIG. 1.
FIG. 3 is a side view of the appliance of FIG. 1.
FIG. 4 is a top plan view of the appliance of FIG. 1.
FIG. 5 is a rear or lingual elevational view of the appliance of FIG. 1.
FIG. 6 is a vertical sectional view taken through the appliance of FIG. 1 generally along line 6—6 thereof.

The appliance 16, in its unstretched state, includes a ring portion or endless strand 24, a diametrically disposed cross member or web 25, and a pair of force transmitting members or nodules 26 and 27 at the lingual or backside and in alignment with the cross member or bar.

The ring portion 24 is cylindrical in cross section, as shown in FIG. 6, although it may be of any suitable geometrical cross section. As seen from the front or back, the ring portion is circular or ring-shaped, although it could take other shapes and still function properly when disposed on a bracket. The cross member portion 25 extends diametrically of the ring portion 24 and is therefore integrally connected at opposite ends with the ring portion. The cross section of the cross member 25 may take any desired form and is shown to be rectangular, as seen in FIG. 6.

The force transmitting members or nodules 26 and 27 of appliance 16 extend only from one side of the appliance and include cylindrical portions or knobs 26a, 27a extending at right angles from the ring portion 24 which may take other geometrical forms.

These nodules additionally include triangular shaped extension portions 26b, 27b in longitudinal alignment with the cross member 25 and extending inwardly from the vertical portions 26a, 27a to generally coact therewith in forming wedge-shaped portions that function as force transmitting devices. The nodules 26 and 27 therefore extend inwardly from the ring portion along the cross member terminating short of the center of the cross member, although they may extend all the way to the center if so desired. These nodules are likewise integrally formed with the ring portion and cross member portion.

The entire appliance 16 will be molded of any suitable resilient or elastic material capable of applying the desired functions of connecting an archwire to a bracket and developing bracket moving forces for assisting in the moving of a bracket relative to the archwire. Thus, the appliance will be generally elastomeric in nature and of a material that will withstand the environment of the mouth and the forces applied between the archwire and the bracket to achieve the desired orthodontic treatment. The appliance may be made entirely of an elastomeric material having the same resilience, or where it includes nodules, the nodules may be made of a material that is less resilient than the ring portion.

It will be further appreciated that the appliance will be sized to properly fit on the orthodontic bracket for which it is to be used, whether it be one of the single tie wing or double tie wing type, or one having one or more tie wing tips on each side of the archwire slot, and so that in its mounted position it will be stretched to apply the desired tension to achieve the functions of connecting the archwire to a bracket and defining supplementary moving forces.

While the appliance of the present invention is illustrated in use on a bracket capable of accommodating both tipping and uprighting movements, it will be appreciated that it may be used on other types of brackets.

The bracket 20 shown in FIGS. 8 to 12 includes a single tie wing 29 having upper and lower tie wing tips 30 and 31 respectively with a horizontally outwardly opening archwire slot defined by diagonally disposed uprighting surfaces or stops 32 and 33 and diagonally disposed tipping surfaces or stops 34 and 35. While the uprighting and tipping surfaces or stops generally function to limit uprighting and tipping movements of a tooth, their detailed operation may be further understood by reference to the aforementioned copending application.

Figure 7:
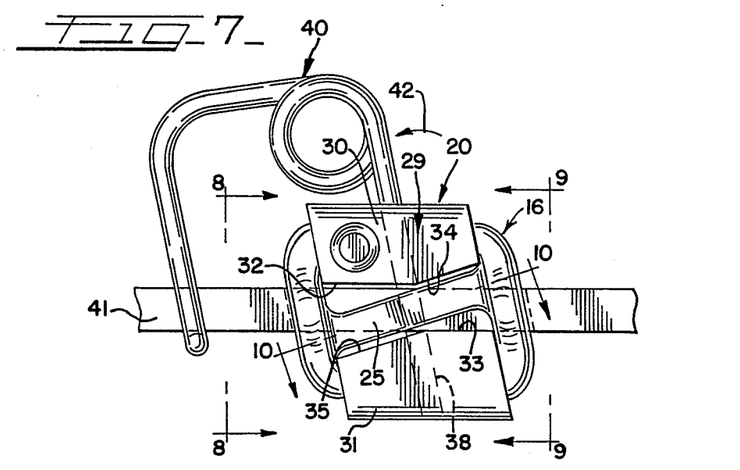
FIG. 7 is a front or labial elevational view of a bracket capable of permitting tipping or uprighting movement along an archwire as it would appear in the mouth of a patient and mounted on a tooth, an archwire disposed in the archwire slot of the bracket, an uprighting spring mounted between the bracket and the archwire, and an elastic orthodontic appliance of the present invention as mounted on the bracket for connecting the archwire to the bracket and for producing additional or supplementary moving forces to supplement the uprighting forces of the uprighting spring.

A vertical slot 38 is provided in the bracket for purposes of anchoring one end of an uprighting spring. As shown in FIG. 7, an uprighting spring 40 anchored at one end in the slot 38 and hooked over the archwire 41 at its other end serves to generate an uprighting force between the bracket and the archwire in the direction of the arrow 42. The archwire 41 is illustrated as being rectangular, but it will be appreciated that a round archwire may be used as illustrated by the archwire 43 in FIG. 12. Normally, a round archwire would be used for tipping, while a rectangular archwire would be used for uprighting and/or torquing. However, a round archwire can be used for uprighting, and a rectangular wire could be used for tipping.

The archwire 41 is shown disposed in the archwire slot of the bracket 20 and the bracket is shown relative to the archwire in its final uprighted position where the uprighting stops 32 and 33 abut against the archwire 41. Before the uprighting action is commenced, it will be appreciated that the bracket 20 would normally be at a position where the uprighting stops would be spaced from the archwire and then the uprighting force would move the bracket until the uprighting stops engage the archwire. The view in FIG. 7 is one where normally the upper tie wing tip 30 would constitute the gingival wing tip as it would be nearest to the gum line, while the lower tip 31 would constitute the occlusal wing tip as it would be nearest to the occlusal. It will be appreciated that the bracket may be mounted on an upper or a lower tooth depending upon the need for use in moving a tooth.

Figure 8:
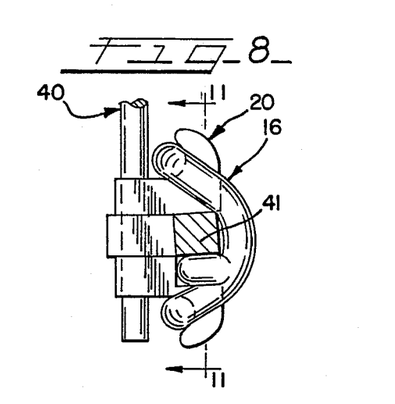
FIG. 8 is an end elevational view of the bracket, wire and appliance assembly of FIG. 7 with some parts removed for purposes of clarity and to illustrate particularly the position of one force nodule between the archwire and a tipping surface of the bracket, taken generally along line 8—8 of FIG. 7.
Figure 9:
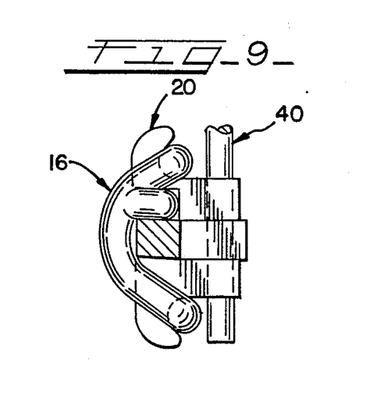
FIG. 9 is a vertical end elevational view like FIG. 8 and taken from the opposite side generally along line 9—9 of FIG. 7 to illustrate the position of the other force nodule between the tipping surface of the bracket and the archwire.
Figure 10:
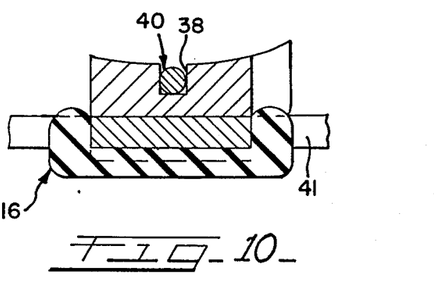
FIG. 10 is a sectional view taken through the assembly of FIG. 7 substantially along line 10—10 thereof.
Figure 11:
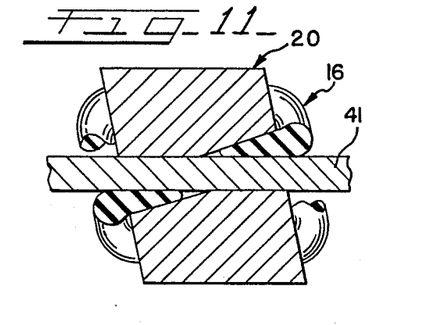
FIG. 11 is a vertical sectional view taken through the assembly and substantially along line 11—11 of FIG. 8.

Application of the elastic orthodontic appliance to the bracket 20 is such that it is hooked over the backsides of both the upper and lower tips, as illustrated, with portions extending along both the mesial and distal sides of the bracket and over the archwire, as seen in FIGS. 7 to 9. In this respect, the appliance functions as an elastic ligature to connect the archwire to the bracket.

Where uprighting is desired, the appliance is mounted on the bracket so that the force transmitting nodules or members 26 and 27 are disposed between the archwire 41 and their respective sides of the bracket contiguous to the tipping surfaces or stops 34 and 35; and depending on the relationship between the bracket and the archwire, the nodules will be seeking to enter between the archwire and the tipping stops or at least be partially between the stops and the archwire. Thus, the nodules would apply forces between the lateral sides of the tie wings and the archwire until movement occurs that would permit the nodules to begin "nosing" between one of the faces of the archwire slot and the archwire. As seen particularly in FIGS. 8 and 9, the knob portions of the nodules coact with the adjacent portion of the ring to provide a force between the archwire and the sides of the bracket. This action of the appliance will supplement the uprighting action of the uprighting spring 40. Further, if the uprighting spring is removed, the force transmitting nodules will be the only force to continue uprighting movement or maintain the position of the bracket, and in this sense they serve as a backup to the uprighting spring. The cross member 25 will also be in a stretched condition as is the ring portion when on a bracket and will therefore tend to pull the force transmitting nodules inward into the space between the archwire and the tipping surfaces of the bracket. Thus, the cross member, together with the force transmission nodules, will serve to supplement the uprighting force generated by the uprighting spring.

Since the appliance is very small and on the order of three to four millimeters in size, the cross member additionally serves to assist the orthodontist in determining the proper positions of the force transmission nodules when mounted on the bracket. Also, the cross bar prevents the ring from twisting along its entire length during placement. If the ring were free to twist, it would be necessary to have the nodules project in all directions from the ring, and as such would result in an unnecessarily bulky, high-profile assembly, as in the prior art.

In order to mount the appliance on a bracket and archwire so that the nodules assist in the uprighting, the cross member is aligned with the tipping stops 34 and 35, as seen in FIG. 7. When it is desired to use the force transmission nodules to assist tipping action, the cross member is aligned with the uprighting surfaces 32 and 33 as illustrated in FIG. 12, where then the nodules will be disposed between the archwire and the sides of the tie wing contiguous to the uprighting stops to produce a force in the direction of the arrow 47. For tipping, another primary force is usually applied, such as by a standard elastic. Again, the orthodontist, by observing the position of the cross member, can readily determine the location of the force transmission nodules which are not readily visible from the front as they extend only from the back of the appliance.

The elastic appliance of the invention may likewise be used on a twin tie wing bracket, as illustrate din FIG. 13, which includes spaced tie wings 50 and 51, each of which includes an archwire slot in alignment with each other and which is defined by uprighting stops or surfaces 52 and 53 and tipping surfaces or stops 54 and 55. The elastic orthodontic appliance 16 of the invention is illustrated in mounting relation on the bracket and oriented to facilitate uprighting action by disposing the cross member 25 in alignment with the tipping stops 54 and 55 and the force transmitting nodules 26 and 27 between the archwire and respectively the tipping surfaces 54 and 55 to cause a counter-clockwise force to be applied to the bracket in the direction of the arrow 56.

Figure 14:
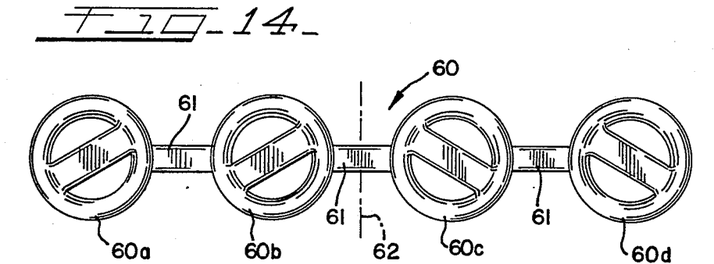
FIG. 14 is a front elevational view of a modification of the invention and illustrating the elastic appliance in chain form.

The elastic appliance of the invention may also be provided in chain form, as shown in FIG. 14, so that the appliance may be used individually or in plural as needed. The chain form appliance is generally indicated by the numeral 60 and would include spaced apart appliances 60a, 60b, 60c and 60d interconnected by a filament or link 61 of the same material as the appliances. Any number of the appliances may be connected together in chain form. Orientation of the cross bar will vary according to the function desired. As shown in FIG. 14, the group is particularly useful to connect the anterior centrals and laterals, so the cross bars on one side of the midline 62 are inclined to the links 61 in one direction and on the other side in the mirror image. However, the orientation of the appliances 60a and 60b may be otherwise, if so desired, such as shown in FIG. 15 where the cross bars of the chain form appliance 63 are coaxial with the connecting links. While the links 61 are shown to appear horizontally, they may also be arranged on an incline between elastic appliances. When in chain form, it will provide the orthodontist with the option of cutting away the links so that each appliance may be used individually or utilizing the links to apply additional forces between adjacent teeth when the appliances are mounted on brackets for those adjacent teeth.

The embodiment of FIGS. 16 to 18, generally designated by the numeral 65, differs from the form shown in the other figures in that it does not include any nodules and in that the ring portion or endless strand 66 is provided with a larger cross member or bar 67 having a slightly projecting relatively pointed portion 68 that faces lingually when mounted on the bracket and seeks to enter between the archwire and the bracket, as seen in FIG. 18. More particularly, the portion 68 will seek to move between the archwire and the tipping or uprighting surfaces, depending upon whether the cross bar is essentially aligned with the tipping or uprighting surfaces, and respectively generate uprighting or tipping forces. This embodiment is illustrated in mounted relation on a single tie wing bracket and for connecting the archwire to the bracket and also for applying a supplementary tipping or uprighting force. In FIG. 18 the portion 68 applies a force between the tipping surfaces and the archwire to urge the bracket to the uprighted position.

It will further be appreciated that the elastic appliance of the present invention may be made with a single nodule or any number of nodules on each side of the ring. A single nodule appliance is illustrated in FIG. 19, where the appliance 70 is defined by a ring portion 71, a diametrical cross bar 72, and a force transmitting nodule 73. The cross bar 72 is tapered along its length, rather than being of uniform cross section as in the other embodiments.

Also, the cross sections of the cross bars may take other geometrical shapes than the ones illustrated. For example, they may be diamond, triangular, or round in cross section, as well as being generally rectangular as illustrated.

Figure 21:
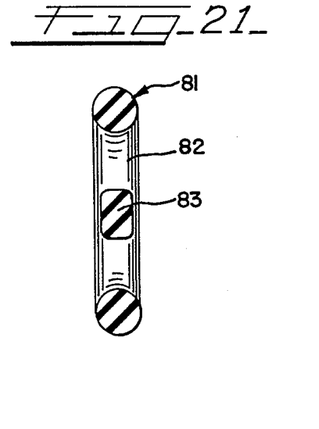
FIG. 21 is a transverse sectional view taken through the appliance of FIG. 20 and generally along the line 21—21 thereof.
Figure 22:
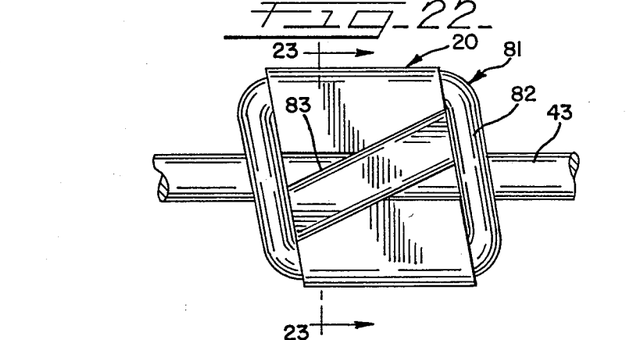
FIG. 22 is a front elevational view of the appliance of FIGS. 20 and 21 mounted in place on a bracket having an archwire received in the archwire groove.
Figure 23:
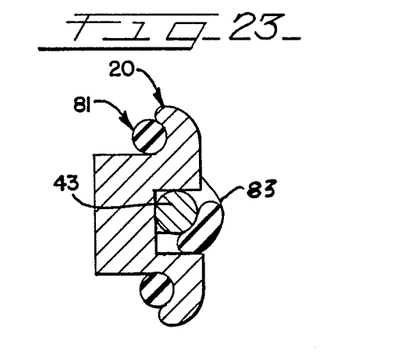
FIG. 23 is an end elevational view of the bracket wire and appliance of FIGS. 20 to 22 but illustrating the use of rectangular wire.
Figure 24:
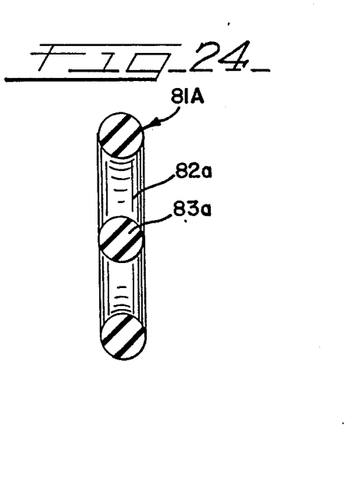
FIG. 24 is a vertical sectional view taken through a modified appliance differing from that of FIGS. 20 and 21 only in that the cross section of the web or cross member is cylindrical instead of being rectangular.

A further embodiment of the invention is shown in Figs. 20 to 23 and generally designated by the numeral 81, which primarily differs from the previous embodiment in that it is lugless or nodule-less, and further that the cross member or web is sized to be coplanar with the ring portion when the appliance is in unstretched condition, as particularly seen in FIG. 21. So, appliance 81 includes a ring portion 82 and a cross member or web 83. While the cross member or web can be of any desired geometrical cross section, it is shown to be rectangular in the appliance. It will be appreciated that the appliance 81 is suitable for retaining an archwire in place on single or double wing brackets, while additionally functioning to apply a supplementary or uprighting force when the cross member is arranged so that it can engage between the archwire and a bracket archwire slot surface such as illustrated in FIGS. 22 and 23. The appliance 81 is illustrated on a single wing bracket 20 in FIGS. 22 and 23, and for retaining a round archwire in the archwire slot of the bracket in FIG. 22 and a rectangular archwire in the archwire slot in the bracket of FIG. 23. It will be appreciated that the areas of the cross member interconnecting with the endless strand or ring portion 82 would be urged into the area between the bracket and the archwire as that part of the strand that goes behind the wings tends to pull the web lingual, while the cross member tends to pull those parts of the strand at the mesial and distal sides of the bracket in tight against the bracket sides. As seen in FIG. 23, a portion of the cross member is engaging between the archwire and the bracket. While the sides of the cross member may be of any desired width or height, it should be of sufficient size to wedge between the wire and tip or uprighting surfaces of the bracket in order to separate the wire and the bracket, or in other words to apply a force between the wire and the adjacent edges or surfaces of the bracket. While illustrated in FIG. 22 as being relatively wide along the vertical, it could be a lesser width and still function to apply a separating force between the archwire and the bracket.

It will be appreciated that the cross section of the web may vary, and as shown by the embodiments 81A in FIG. 24, the cross member 83a is cylindrical in shape and also has a diameter substantially equal to the diameter of the ring portion. Further, it will be appreciated that the ring portion or endless strand in unstretched condition may be shaped as a ring or donut, as illustrated herein, or it may be oval, triangular, rectangular, polygonal, or otherwise shaped. This illustrates the different type of geometrical shape that can be used for the cross member. Other than as already explained, the appliances 81 and 81A will function as described relative to the previous appliances insofar as applying a separate force between the archwire and the adjacent bracket surfaces.

While not shown, the appliance of the invention could also be used with a standard elastic ligature, where the appliance would be mounted onto the bracket ahead of the archwire and in a reversed position with the nodules portion facing outwardly. The cross bar would be disposed in the archwire slot and the ring portion would be behind the tie wing tips and along opposite sides of the bracket. Then, the archwire would be disposed in the slot over the cross bar and so the nodule or nodules would be disposed between the archwire and the bracket. A standard elastic ligature would then be mounted to hold the archwire in place.

From the foregoing, it will be appreciated that the elastic appliance of the present invention with the unique cross bar or member greatly facilitates treatment and greatly supplements the tipping or uprighting forces needed during use of the brackets illustrated.

It will be understood that modifications and variations may be effected without departing from the scope of the novel concepts of the present invention, but it is understood that this application is to be limited only by the scope of the appended claims.

The invention is hereby claimed as follows:

1. An elastic appliance for an edgewise-type bracket to retain an archwire in the archwire slot of said bracket and to transmit a force between the archwire and bracket to cause said bracket and a tooth on which it is mounted to move or stabilize relative to said archwire, said appliance in unstretched condition comprising a ring portion, a cross member portion diametrical to said ring portion, and at least one force transmitting portion extending from said ring portion and cross member portion and in alignment with said cross member portion, whereby said ring portion functions to retain an archwire on a bracket and said force transmitting portion is held in place by said cross member between the archwire and the bracket to function as force transmitting means between the archwire and bracket.

2. The appliance of claim 1, wherein said force transmitting portion extends from one side of said ring and cross member portions.

3. The appliance of claim 2, wherein said force transmitting portion is wedge-shaped.

4. The appliance of claim 1, wherein a pair of force transmitting portions are provided, one at each end of said cross member portion.

5. The appliance of claim 1, wherein a single force transmitting portion extends from one side of said ring and cross member portion.

6. An elastic orthodontic appliance for retaining an archwire on an edgewise-type bracket and for applying a tipping force between the archwire and bracket to induce movement or control between the archwire and the bracket, wherein said bracket includes at least one tie wing with occlusal and gingival tips and a horizontally opening archwire slot in said tie wing having diagonally disposed tipping surfaces and diagonally disposed uprighting surfaces, said appliance comprising an endless strand for hooking over and behind said tips and having portions extending along the mesial and distal sides of said bracket and over an archwire disposed in said slot, a cross member extending between said strand portions, and enlargements along said cross member at the backside thereof for disposition between the archwire and the bracket, said enlargements being sized relative to the archwire and bracket to be compressed when activated thereby generating a force to induce movement of the bracket relative to the archwire.

7. The appliance of claim 6, wherein said enlargements are wedge-shaped.

8. The appliance of claim 7, wherein said enlargements extend from one side of the appliance.

9. The appliance of claim 8, wherein said enlargements include one disposed at each end of the cross member.

10. The appliance of claim 6, wherein the resilience of the enlargements is less than that of the endless strand.

11. In combination with an edgewise-type bracket having at least one tie wing with occlusal and gingival tips and a horizontally opening archwire slot including diagonally disposed tipping surfaces and diagonally disposed uprighting surfaces, an archwire in said slot, an elastic appliance having an endless strand looped over and behind said tips and extending along opposite sides of the bracket and over said archwire in stretched condition, a cross member connected to said strand and disposed over said archwire and in said slot, and force means in alignment with said cross member and/or disposed between said archwire and said bracket tipping surfaces to generate an uprighting force.

12. The elastic appliance of claim 11, wherein said force means is wedge-shaped.

13. The elastic appliance of claim 11, wherein said force means includes a single nodule extending from one side of said appliance.

14. The elastic appliance of claim 11, wherein said force means includes a plurality of nodules extending from one side of said appliance.

15. The elastic appliance of claim 11, wherein a plurality of appliances are interconnected in chain form.

16. In combination with an edgewise-type bracket having at least one tie wing with occlusal and gingival tips and a horizontally opening archwire slot including diagonally disposed uprighting surfaces and diagonally disposed tipping surfaces, an archwire in said slot, an elastic appliance having an endless strand looped over and behind said tips and extending along opposite sides of the bracket over said archwire in stretched condition to connect the archwire and bracket, a cross member disposed over said archwire and extending between the portions of said endless strand at opposite sides of said bracket, and wedge means extending from said strand and cross member and in alignment with said cross member and disposable between said archwire and the side of the bracket wing tip contiguous to said uprighting surfaces or said archwire and the side of the bracket wing tip contiguous to said tipping surfaces to apply a force therebetween, whereby said cross member urges said wedge means toward and between said archwire and uprighting or tipping surfaces.

17. An elastic appliance for and edgewise-type bracket to retain an archwire in the archwire slot of said bracket and to transmit a force between the archwire and bracket to cause said bracket and a tooth on which it is mounted to move and/or stabilize relative to said archwire, said appliance in unstretched condition comprising a ring portion, a cross member portion diametrical to said ring portion, said cross member having a portion projecting from the backside with a cross-sectional wedge shape that seeks to move between the archwire and the bracket, whereby said appliance functions to retain an archwire on a bracket and exert a force between the archwire and the bracket.

18. In combination with an edgewise-type bracket having at least one tie wing with occlusal and gingival tips and a horizontally opening archwire slot including at least one uprighting surface and at least one tipping surface, an archwire in said slot, an elastic appliance having an endless strand looped behind said tips and extending along opposite sides of the bracket over said archwire in stretched condition to connect the archwire and bracket, a cross member disposed across said archwire and extending between the portions of said endless strand at opposite sides of said bracket, and said cross member having a wedge shape in cross section portion projecting from the side of the cross member facing the bracket and seeking to move between the archwire and the uprighting or tipping surfaces.

19. In combination with an edgewise-type bracket having at least one tie wing with occlusal and gingival tips and a horizontally opening archwire slot including diagonally disposed uprighting surfaces and diagonally disposed tipping surfaces, an archwire in said slot, an elastic appliance having an endless strand looped behind said tips and extending along opposite sides of the bracket over said archwire in stretched condition to connect the archwire and bracket, a cross member disposed across said archwire and extending between the portions of said endless strand at opposite sides of said bracket, and said cross member having a wedge shape in cross section portion projecting from the side of the cross member facing the bracket and seeking to move between the archwire and the uprighting or tipping surfaces.

20. An elastic appliance for an edgewise-type bracket retaining an archwire in the archwire slot of an edgewise-type bracket in overlying relation to said archwire to transmit a force between the archwire and bracket to cause said bracket and a tooth on which it is mounted to move and/or stabilize relative to said archwire, said appliance in unstretched condition comprising an endless strand portion, and a cross member portion integral with and extending across the strand portion, whereby said appliance functions to retain an archwire on a bracket and exert a force between the archwire and the bracket.

21. In combination with an edgewise-type bracket having at least one tie wing with occlusal and gingival tips and a horizontally opening archwire slot including at least one uprighting surface and at least one tipping surface, an archwire in said slot, an elastic appliance having an endless strand looped behind said tips and extending along opposite sides of the bracket over said archwire in stretched condition to connect the archwire and bracket, and a cross member disposed across said archwire and extending between the portions of said endless strand at opposite sides of said bracket, whereby said cross member at said portions seeks to move between the archwire and the uprighting or tipping surfaces to apply a separating force.

22. In combination with an edgewise-type bracket having at least one tie wing with occlusal and gingival tips and a horizontally opening archwire slot including diagonally disposed uprighting surfaces and diagonally disposed tipping surfaces, an archwire in said slot, an elastic appliance having an endless strand looped behind said tips and extending along opposite sides of the bracket over said archwire in stretched condition to connect the archwire and bracket, and a cross member disposed across said archwire and extending between the portions of said endless strand at opposite sides of said bracket, whereby said cross member at said portions seeks to move between the archwire and the uprighting or tipping surface to apply a separating force.

23. An elastic orthodontic appliance in an overlying relation with and retaining an archwire on an edge-wise bracket and applying a tipping force between the archwire and bracket to induce movement or control between the archwire and the bracket, wherein said bracket includes at least one tie wing with occlusal and gingival tips and a horizontally opening archwire slot in said tie wing having diagonally disposed tipping surfaces and diagonally disposed uprighting surfaces, said appliance comprising an endless strand for hooking over and behind said tips and having portions extending along the mesial and distal sides of said bracket and over an archwire disposed in said slot, and a cross member extending between said strand portions.

24. The appliance of claim 23, wherein said cross member is coplanar with said endless strand when the appliance is in its unstretched condition.

25. The appliance of claim 23, wherein said cross member is aligned with said archwire slot.

26. The appliance of claim 23, wherein said cross member is of sufficient size to wedge between the archwire and adjacent bracket surface to produce a separating force between the archwire and bracket.

* * * * *